United States Patent
Clauda

(10) Patent No.: US 11,229,473 B2
(45) Date of Patent: Jan. 25, 2022

(54) COMBINATION ULTRASONIC AND ELECTROSURGICAL INSTRUMENT WITH CLAMP ARM POSITION INPUT AND METHOD FOR IDENTIFYING TISSUE STATE

(71) Applicant: Ethicon LLC, Guaynabo, PR (US)

(72) Inventor: Phillip H. Clauda, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 573 days.

(21) Appl. No.: 15/967,758

(22) Filed: May 1, 2018

(65) Prior Publication Data

US 2018/0333182 A1    Nov. 22, 2018

Related U.S. Application Data

(60) Provisional application No. 62/509,336, filed on May 22, 2017.

(51) Int. Cl.
*A61B 18/14* (2006.01)
*A61B 18/00* (2006.01)
(Continued)

(52) U.S. Cl.
CPC ...... *A61B 18/00* (2013.01); *A61B 17/320092* (2013.01); *A61B 18/1233* (2013.01);
(Continued)

(58) Field of Classification Search
CPC .... A61B 17/320068; A61B 17/320092; A61B 2017/00026; A61B 2017/00084;
(Continued)

(56) References Cited

U.S. PATENT DOCUMENTS 5,322,055 A    6/1994  Davison et al.
5,792,135 A    8/1998  Madhani et al.
(Continued)

FOREIGN PATENT DOCUMENTS

EP    1 839 599 A1    10/2007

OTHER PUBLICATIONS

International Search Report and Written Opinion for International Application No. PCT/US2018/033301, dated Jul. 30, 2018, 13 pgs.
(Continued)

*Primary Examiner* — Khadijeh A Vahdat
(74) *Attorney, Agent, or Firm* — Frost Brown Todd LLC

(57) ABSTRACT

An ultrasonic surgical instrument and method for identifying tissue state and energizing the surgical instrument includes an end effector having an ultrasonic blade and an RF electrode, a shaft assembly, a body, and a power controller. A first ultrasonic energy input is configured to be actuated from a first unactuated energy input state to a first actuated energy input state. A trigger input is configured to be actuated from an unactuated trigger input state to an actuated trigger input state. The power controller is operatively connected to the ultrasonic blade, the RF electrode, the first ultrasonic energy input, and the trigger input and configured to direct at least one of the ultrasonic blade or the RF electrode to be selectively driven according to a predetermined drive function based on the tissue impedance, the state of the first energy input, and the state of the trigger input.

20 Claims, 6 Drawing Sheets

(51) Int. Cl.
*A61B 17/32* (2006.01)
*A61B 18/12* (2006.01)
A61B 17/00 (2006.01)
A61B 90/00 (2016.01)

(52) U.S. Cl.
CPC .. *A61B 18/1445* (2013.01); *A61B 2017/0019* (2013.01); *A61B 2017/00026* (2013.01); *A61B 2017/00084* (2013.01); *A61B 2017/00106* (2013.01); *A61B 2017/00526* (2013.01); *A61B 2017/320075* (2017.08); *A61B 2017/320088* (2013.01); *A61B 2017/320094* (2017.08); *A61B 2017/320095* (2017.08); *A61B 2018/0063* (2013.01); *A61B 2018/00607* (2013.01); *A61B 2018/00642* (2013.01); *A61B 2018/00648* (2013.01); *A61B 2018/00654* (2013.01); *A61B 2018/00672* (2013.01); *A61B 2018/00678* (2013.01); *A61B 2018/00702* (2013.01); *A61B 2018/00708* (2013.01); *A61B 2018/00714* (2013.01); *A61B 2018/00755* (2013.01); *A61B 2018/00761* (2013.01); *A61B 2018/00779* (2013.01); *A61B 2018/00875* (2013.01); *A61B 2018/00916* (2013.01); *A61B 2018/00928* (2013.01); *A61B 2018/00994* (2013.01); *A61B 2018/126* (2013.01); *A61B 2018/1452* (2013.01); *A61B 2090/064* (2016.02)

(58) Field of Classification Search
CPC .. A61B 2017/00106; A61B 2017/0019; A61B 2017/00526; A61B 2017/320075; A61B 2017/320088; A61B 2017/320094; 2017/320095; A61B 18/00; A61B 18/12; A61B 18/1233; A61B 18/14; A61B 18/1442; A61B 18/1445; A61B 2018/00607; A61B 2018/0063; A61B 2018/00642; A61B 2018/00648; A61B 2018/00654; A61B 2018/00672; A61B 2018/00678; A61B 2018/00702; A61B 2018/00708; A61B 2018/00714; A61B 2018/00755; A61B 2018/00761; A61B 2018/00779; A61B 2018/00791; A61B 2018/00845; A61B 2018/00875; A61B 2018/0088; A61B 2018/00916; A61B 2018/00928; A61B 2018/00994; 2018/126; A61B 2018/1452; A61B 2018/1457; A61B 2018/1467; A61B 2090/064
USPC .................................................... 606/33–52
See application file for complete search history.

(56) References Cited

U.S. PATENT DOCUMENTS

| | | | |
|---|---|---|---|
| 5,817,084 A | 10/1998 | Jensen |
| 5,873,873 A | 2/1999 | Smith et al. |
| 5,878,193 A | 3/1999 | Wang et al. |
| 5,980,510 A | 11/1999 | Tsonton et al. |
| 6,231,565 B1 | 5/2001 | Tovey et al. |
| 6,283,981 B1 | 9/2001 | Beaupre et al. |
| 6,309,400 B2 | 10/2001 | Beaupre |
| 6,325,811 B1 | 12/2001 | Messerly |
| 6,364,888 B1 | 4/2002 | Niemeyer et al. |
| 6,423,082 B1 | 7/2002 | Houser et al. |
| 6,500,176 B1 | 12/2002 | Truckai et al. |
| 6,773,444 B2 | 8/2004 | Messerly |
| 6,783,524 B2 | 8/2004 | Anderson et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,524,320 B2 | 4/2009 | Tierney et al. |
| 7,691,098 B2 | 4/2010 | Wallace et al. |
| 7,806,891 B2 | 10/2010 | Nowlin et al. |
| 8,057,498 B2 | 11/2011 | Robertson |
| 8,058,771 B2 | 11/2011 | Giordano et al. |
| 8,366,727 B2 | 2/2013 | Witt et al. |
| 8,460,326 B2 | 6/2013 | Houser et al. |
| 8,461,744 B2 | 6/2013 | Wiener et al. |
| 8,479,969 B2 | 7/2013 | Shelton, IV |
| 8,573,461 B2 | 11/2013 | Shelton, IV et al. |
| 8,573,465 B2 | 11/2013 | Shelton, IV |
| 8,591,536 B2 | 11/2013 | Robertson |
| 8,602,288 B2 | 12/2013 | Shelton, IV et al. |
| 8,616,431 B2 | 12/2013 | Timm et al. |
| 8,623,027 B2 | 1/2014 | Price et al. |
| 8,663,220 B2 | 3/2014 | Wiener et al. |
| 8,783,541 B2 | 7/2014 | Shelton, IV et al. |
| 8,800,838 B2 | 8/2014 | Shelton, IV |
| 8,820,605 B2 | 9/2014 | Shelton, IV |
| 8,844,789 B2 | 9/2014 | Shelton, IV et al. |
| 8,939,974 B2 | 1/2015 | Boudreaux et al. |
| 9,044,261 B2 | 6/2015 | Houser |
| 9,089,327 B2 | 7/2015 | Worrell et al. |
| 9,161,803 B2 | 10/2015 | Yates et al. |
| 9,192,431 B2 | 11/2015 | Woodruff et al. |
| 9,301,759 B2 | 4/2016 | Spivey et al. |
| 9,402,682 B2 | 8/2016 | Worrell et al. |
| 9,439,668 B2 | 9/2016 | Timm et al. |
| 9,545,253 B2 | 1/2017 | Worrell et al. |
| 9,572,622 B2 | 2/2017 | Shelton, IV et al. |
| 9,681,884 B2 | 6/2017 | Clem et al. |
| 9,724,118 B2 | 8/2017 | Schulte et al. |
| 10,194,972 B2 | 2/2019 | Yates et al. |
| 10,813,684 B2 | 10/2020 | Worrell et al. |
| 2011/0087212 A1 | 4/2011 | Aldridge et al. |
| 2012/0078243 A1 | 3/2012 | Worrell et al. |
| 2012/0116391 A1 | 5/2012 | Houser et al. |
| 2013/0282003 A1* | 10/2013 | Messerly ........... A61B 18/1206 606/37 |
| 2015/0141981 A1 | 5/2015 | Price et al. |
| 2015/0257780 A1 | 9/2015 | Houser |
| 2016/0022305 A1 | 1/2016 | Lamping et al. |
| 2016/0270840 A1 | 9/2016 | Yates et al. |
| 2016/0310204 A1* | 10/2016 | McHenry ........... A61B 18/1445 |
| 2017/0000516 A1 | 1/2017 | Stulen et al. |
| 2017/0000541 A1 | 1/2017 | Yates et al. |
| 2017/0000542 A1 | 1/2017 | Yates et al. |
| 2017/0000554 A1 | 1/2017 | Yates et al. |
| 2017/0056056 A1 | 3/2017 | Wiener et al. |

OTHER PUBLICATIONS

International Search Report and Written Opinion for International Application No. PCT/US2018/033303, dated Jan. 24, 2019, 20 pgs.
U.S. Appl. No. 62/509,336, entitled "Control Algorithm for Surgical Instrument With Ultrasonic and Electrosurgical Modalities," filed May 22, 2017.
International Search Report and Written Opinion for International Application No. PCT/US2018/033305, dated Aug. 23, 2018, 16 pages.
International Search Report and Written Opinion for International Application No. PCT/US2018/033306, dated Sep. 3, 2018, 17 pages.
International Search Report and Written Opinion for International Application No. PCT/US2018/033309, dated Aug. 17, 2018, 16 pages.
International Search Report and Written Opinion for International Application No. PCT/US2018/033311, dated Aug. 23, 2018, 16 pages.

(56) References Cited

OTHER PUBLICATIONS

U.S. Appl. No. 15/967,740, entitled "Combination Ultrasonic and Electrosurgical Instrument Having Electrical Circuits with Shared Return Path," filed May 1, 2018.
U.S. Appl. No. 15/967,746, entitled "Combination Ultrasonic and Electrosurgical Instrument Having Slip Ring Electrical Contact Assembly," filed May 1, 2018.
U.S. Appl. No. 15/967,747, entitled "Combination Ultrasonic and Electrosurgical Instrument Having Electrically Insulating Features," filed May 1, 2018.
U.S. Appl. No. 15/967,751, entitled "Combination Ultrasonic and Electrosurgical Instrument Having Curved Ultrasonic Blade," filed May 1, 2018.
U.S. Appl. No. 15/967,753, entitled "Combination Ultrasonic and Electrosurgical Instrument Having Clamp Arm Electrode," filed May 1, 2018.
U.S. Appl. No. 15/967,759, entitled "Combination Ultrasonic and Electrosurgical Instrument Having Ultrasonic Waveguide with Distal Overmold Member," filed May 1, 2018.
U.S. Appl. No. 15/967,761, entitled "Combination Ultrasonic and Electrosurgical System Having Generator Filter Circuitry," filed May 1, 2018.
U.S. Appl. No. 15/967,763, entitled "Combination Ultrasonic and Electrosurgical Instrument with Adjustable Energy Modalities and Method for Sealing Tissue and Inhibiting Tissue Resection," filed May 1, 2018.
U.S. Appl. No. 15/967,764, entitled "Combination Ultrasonic and Electrosurgical System Having Eeprom and Asic Components," filed May 1, 2018.
U.S. Appl. No. 15/967,770, entitled "Combination Ultrasonic and Electrosurgical Instrument with a Production Clamp Force Based Ultrasonic Seal Process and Related Methods," filed May 1, 2018.
U.S. Appl. No. 15/967,775, entitled "Combination Ultrasonic and Electrosurgical Instrument with Adjustable Energy Modalities and Method for Limiting Blade Temperature," filed May 1, 2018.
U.S. Appl. No. 15/967,777, entitled "Combination Ultrasonic and Electrosurgical Instrument and Method for Sealing Tissue with Various Termination Parameters," filed May 1, 2018.
U.S. Appl. No. 15/967,784, entitled "Combination Ultrasonic and Electrosurgical Instrument and Method for Sealing Tissue in Successive Phases," filed May 1, 2018.
U.S. Appl. No. 62/509,351, entitled "Ultrasonic Instrument with Electrosurgical Features," filed May 22, 2017.
U.S. Appl. No. 15/967,763.
U.S. Appl. No. 15/967,770.
U.S. Appl. No. 15/967,775.
U.S. Appl. No. 15/967,777.
U.S. Appl. No. 15/967,784.
European Examination Report dated Jun. 28, 2021, for Application No. 18729278.4, 4 pgs.
European Examination Report dated Jun. 29, 2021, for Application No. 18731583.3, 4 pgs.
European Examination Report dated Jun. 29, 2021, for Application No. 18731584.1, 4 pgs.
European Examination Report dated Jun. 30, 2021, for Application No. 18731585.8, 4 pgs.

* cited by examiner

COMBINATION ULTRASONIC AND ELECTROSURGICAL INSTRUMENT WITH CLAMP ARM POSITION INPUT AND METHOD FOR IDENTIFYING TISSUE STATE

CROSS-REFERENCE TO RELATED APPLICATION

This application claims priority to U.S. Provisional Pat. App. No. 62/509,336, entitled "Control Algorithm for Surgical Instrument with Ultrasonic and Electrosurgical Modalities," filed May 22, 2017, the disclosure of which is incorporated by reference herein.

BACKGROUND

Ultrasonic surgical instruments utilize ultrasonic energy for both precise cutting and controlled coagulation. Ultrasonic energy cuts and coagulates by vibrating a blade in contact with tissue. Vibrating at frequencies of approximately 55.5 kilohertz (kHz), for example, the ultrasonic blade denatures protein in the tissue to form a sticky coagulum. Pressure exerted on the tissue with the blade surface collapses blood vessels and allows the coagulum to form a hemostatic seal. The precision of cutting and coagulation may be controlled by the surgeon's technique and adjusting the power level, blade edge, tissue traction, and blade pressure, for example.

Examples of ultrasonic surgical devices include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; U.S. Pat. No. 8,623,027, entitled "Ergonomic Surgical Instruments," issued Jan. 7, 2014, the disclosure of which is incorporated by reference herein; and U.S. Pub. No. 2016/0022305, entitled "Ultrasonic Blade Overmold," published Jan. 28, 2016, issued as U.S. Pat. No. 9,350,521 on Sep. 5, 2017, the disclosure of which is incorporated by reference herein.

Electrosurgical instruments utilize electrical energy for sealing tissue, and generally include a distally mounted end effector that can be configured for bipolar or monopolar operation. During bipolar operation, electrical current is provided through the tissue by active and return electrodes of the end effector. During monopolar operation, current is provided through the tissue by an active electrode of the end effector and a return electrode (e.g., a grounding pad) separately located on a patient's body. Heat generated by the current flowing through the tissue may form hemostatic seals within the tissue and/or between tissues, and thus may be particularly useful for sealing blood vessels, for example. The end effector of an electrosurgical device may also include a cutting member that is movable relative to the tissue and the electrodes to transect the tissue.

Electrical energy applied by an electrosurgical device can be transmitted to the instrument by a generator coupled with the instrument. The electrical energy may be in the form of radio frequency ("RF") energy, which is a form of electrical energy generally in the frequency range of approximately 300 kilohertz (kHz) to 1 megahertz (MHz). In use, an electrosurgical device can transmit such energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy works particularly well on connective tissue, which is primarily comprised of collagen and shrinks when contacted by heat.

An example of an RF electrosurgical device is the ENSEAL® Tissue Sealing Device by Ethicon Endo-Surgery, Inc., of Cincinnati, Ohio. Further examples of electrosurgical devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical devices and related concepts are disclosed in U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein; U.S. Pat. No. 9,161,803, entitled "Motor Driven Electrosurgical Device with Mechanical and Electrical Feedback," issued Oct. 20, 2015, the disclosure of which is incorporated by reference herein; U.S. Pub. No. 2012/0078243, entitled "Control Features for Articulating Surgical Device," published Mar. 29, 2012, issued as U.S. Pat. No. 9,877,720 on Jan. 30, 2018, the disclosure of which is incorporated by reference herein; U.S. Pat. No. 9,402,682, entitled "Articulation Joint Features for Articulating Surgical Device," issued Aug. 2, 2016, the disclosure of which is incorporated by reference herein; U.S. Pat. No. 9,089,327, entitled "Surgical Instrument with Multi-Phase Trigger Bias," issued Jul. 28, 2015, the disclosure of which is incorporated by reference herein; U.S. Pat. No. 9,545,253, entitled "Surgical Instrument with Contained Dual Helix Actuator Assembly," issued Jan. 17, 2017, the disclosure of which is incorporated by reference herein; and U.S. Pat. No. 9,572,622, entitled "Bipolar Electrosurgical Features for Targeted Hemostasis," issued Feb. 21, 2017, the disclosure of which is incorporated by reference herein.

Some instruments may provide ultrasonic and RF energy treatment capabilities through a single surgical device. Examples of such devices and related methods and concepts are disclosed in U.S. Pat. No. 8,663,220, entitled "Ultrasonic Surgical Instruments," issued Mar. 4, 2014, the disclosure of which is incorporated by reference herein; U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and U.S. Pub. No. 2017/0000541, entitled "Surgical Instrument with User Adaptable Techniques," published Jan. 5, 2017, issued as U.S. Pat. No. 11,141,213 on Oct. 12, 2021, the disclosure of which is incorporated by reference herein.

While various types of ultrasonic surgical instruments and electrosurgical instruments, including combination ultrasonic-electrosurgical devices, have been made and used, it is believed that no one prior to the inventor(s) has made or used the invention described herein.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
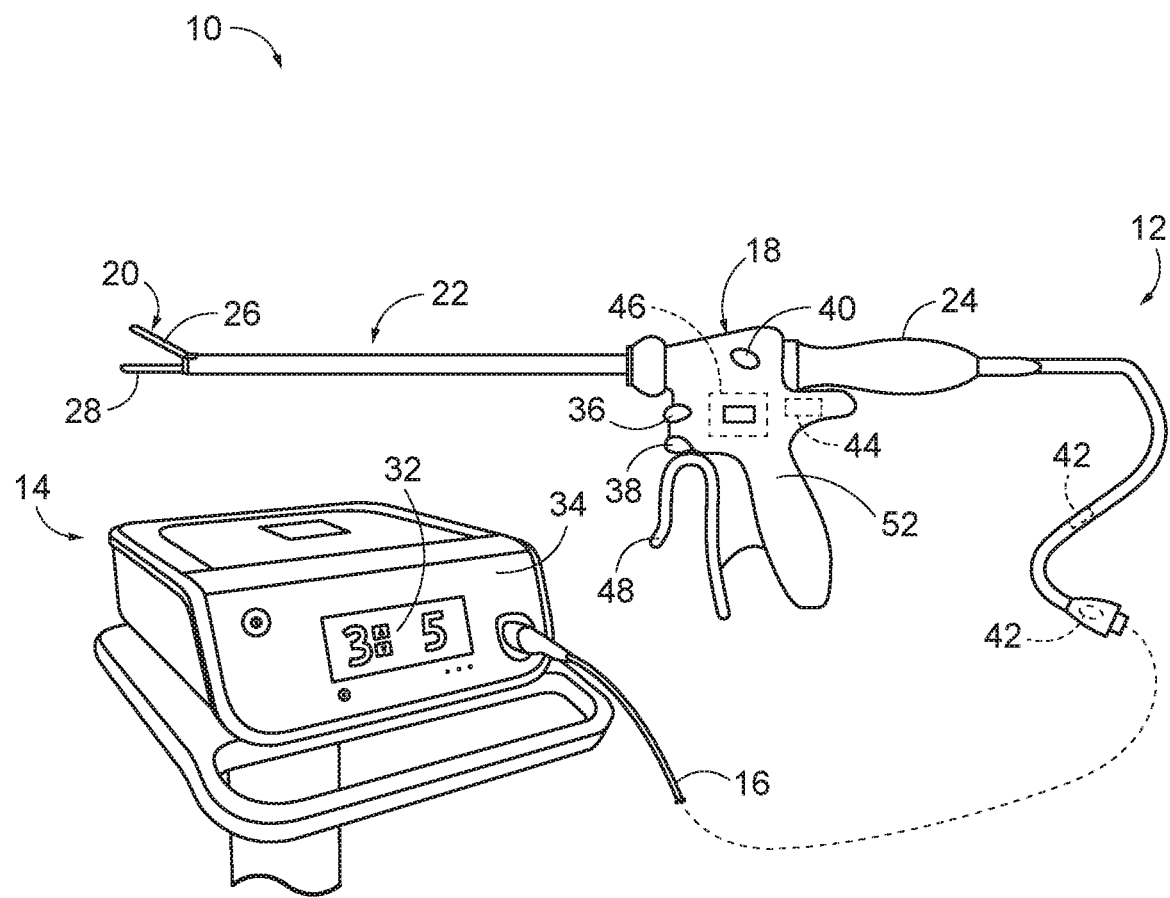
FIG. 1 depicts a schematic view of an exemplary ultrasonic surgical instrument including a shaft assembly and a handle assembly operatively connected to an ultrasonic generator.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical System

FIG. 1 illustrates one example of a surgical system (10) including a surgical instrument (12) and a generator (14) coupled via a cable (16). Surgical instrument (12) has a proximally positioned handle assembly (18), which may also be referred to as a handpiece, a distally positioned end effector (20), a shaft assembly (22) extending therebetween, and an ultrasonic transducer (24). End effector (20) generally includes a clamp arm (26) pivotally connected relative to an ultrasonic blade (28) and configured to pivot from an open position of an open configuration to a closed position of a closed configuration as discussed below in greater detail. Ultrasonic blade (28) is acoustically coupled with ultrasonic transducer (24) via an acoustic waveguide (not shown) for providing ultrasonic energy to ultrasonic blade (28). In addition, end effector (20) further includes a plurality of RF electrodes (30) positioned therealong for contacting the tissue in either the open or closed position as desired by a clinician. Generator (14) operatively connects to ultrasonic blade (28) and RF electrodes (30) to respectively provide ultrasonic energy and RF energy to ultrasonic blade (28) and RF electrodes (30) to thereby cut and/or seal the tissue is use.

In some versions, clamp arm (26) has two or more electrodes (30). In some such versions, electrodes (30) of clamp arm are capable of applying bipolar RF energy to tissue. In some such versions, ultrasonic blade (28) remains electrically neutral, such that ultrasonic blade (28) is not part of the RF circuit. In some other versions, ultrasonic blade (28) forms part of the RF circuit, such that ultrasonic blade (28) cooperates with one or more electrodes (30) of clamp arm (26) to apply bipolar RF energy to tissue. By way of example only, some versions of clamp arm (26) may have just one electrode (30) that serves as an active pole for RF energy; while ultrasonic blade (28) provides a return pole for RF energy. Thus, the term "electrodes (30)" should be read to include versions where clamp arm (26) has only one single electrode.

It should be understood that terms such as "proximal" and "distal" are used herein with reference to surgical instrument (12). Thus, end effector (20) is distal with respect to the more proximal handle assembly (18). It will be further appreciated that for convenience and clarity, spatial terms such as "upper" and "lower" are used herein with respect to the drawings. However, surgical instruments are used in many orientations and positions, and these terms are not intended to be limiting and absolute. Likewise, terms such as "instrument" and "device" as well as "limit" and "cap" may be used interchangeably.

A. Exemplary Generator

With reference to FIG. 1, generator (14) drives a combination surgical instrument (12) with both ultrasonic and RF energies. Generator (14) is shown separate from surgical instrument (12) in the present example, but, alternatively, generator (14) may be formed integrally with surgical instrument (12) to form a unitary surgical system. Generator (14) generally includes an input device (32) located on a front panel (34) of generator (14). Input device (32) may have any suitable device that generates signals suitable for programming the operation of generator (32). For example, in operation, the clinician may program or otherwise control operation of generator (32) using input device (32) (e.g., by one or more processors contained in the generator) to control the operation of generator (14) (e.g., operation of the ultrasonic generator drive circuit (not shown) and/or RF generator drive circuit (not shown)).

In various forms, input device (32) includes one or more buttons, switches, thumbwheels, keyboard, keypad, touch screen monitor, pointing device, remote connection to a general purpose or dedicated computer. In other forms, input device (32) may having a suitable user interface, such as one or more user interface screens displayed on a touch screen monitor. Accordingly, the clinician may selectively set or program various operating parameters of the generator, such as, current (I), voltage (V), frequency (f), and/or period (T) of a drive signal or signals generated by the ultrasonic and RF generator drive circuits (not shown). Specifically, in the present example, generator (32) is configured to deliver various power states to the surgical instrument (10) that include, but are not necessarily limited to, only ultrasonic energy, only RF energy, and a combination of ultrasonic and RF energies, which simultaneously powers ultrasonic blade (28) and RF electrodes (30). It will be appreciated that input device (32) may have any suitable device that generates signals suitable for programming the operation of generator (14) and should not be unnecessarily limited to input device (32) shown and described herein.

By way of example only, generator (14) may comprise a GEN04 or GEN11 sold by Ethicon Endo-Surgery, Inc. of Cincinnati, Ohio. In addition, or in the alternative, generator (14) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein.

B. Exemplary Surgical Instrument

Surgical instrument (10) of the present example shown in FIG. 1 includes a plurality of energy inputs, which are more particularly referred to herein as an upper button (36), lower button (38), and side button (40). By way of example, upper button (36) is configured to direct generator (14) to power ultrasonic transducer (24) with a maximum ultrasonic energy output, whereas lower button (38) is configured to direct generator (14) to power ultrasonic transducer (24) with a lower ultrasonic energy output. By way of further example, side button (40) is configured to direct generator (14) to power ultrasonic transducer (24) with a pulsed energy output, such as 5 continuous signals and 5 or 4 or 3 or 2 or 1 pulsed signals. In one or more examples, the specific drive signal configuration directed by energy inputs may be controlled and/or based upon EEPROM settings in generator (14) and/or user power level selection(s). By way of further example, surgical instrument (10) may include a two-button configuration for selectively directing ultrasonic and RF energies as described herein. Various examples of instruments having two-button input configurations are described in various patent references cited herein. In any case, it will be appreciated that the invention described herein is not intended to be unnecessarily limited to a particular input button, switch, etc. to the extent that any form of input may be so used.

Surgical instrument (12) further includes a first data circuit (42) and a second data circuit (44) in communication with generator (14). For example, first data circuit (42) indicates a burn-in frequency slope. Additionally or alternatively, any type of information may be communicated to second data circuit (42) for storage therein via a data circuit interface (e.g., using a logic device). Such information may comprise, for example, an updated number of operations in which surgical instrument (12) has been used and/or dates and/or times of its usage. In other examples, second data circuit (44) may transmit data acquired by one or more sensors (e.g., an instrument-based temperature sensor). In still other examples, second data circuit (44) may receive data from generator (14) and provide an indication to a clinician (e.g., an LED indication or other visible indication) based on the received data to and/or from surgical instrument (12). In the present example, second data circuit (44) stores information about the electrical and/or ultrasonic properties of an associated transducer (24) and/or end effector (20), which includes data measured and collected from ultrasonic blade (28) and/or RF electrodes (30).

To this end, various processes and techniques described herein are performed by a controller (46), which includes internal logic. In one example, controller (46) has at least one processor and/or other controller device in communication with generator (14), ultrasonic blade (28), RF electrodes (30), and other inputs and outputs described herein for monitoring and performing such processes and techniques. In one example, controller (46) has a processor configured to monitor user input provided via one or more inputs and capacitive touch sensors. Controller (46) may also include a touch screen controller to control and manage the acquisition of touch data from a capacitive touch screen.

Figure 2A:
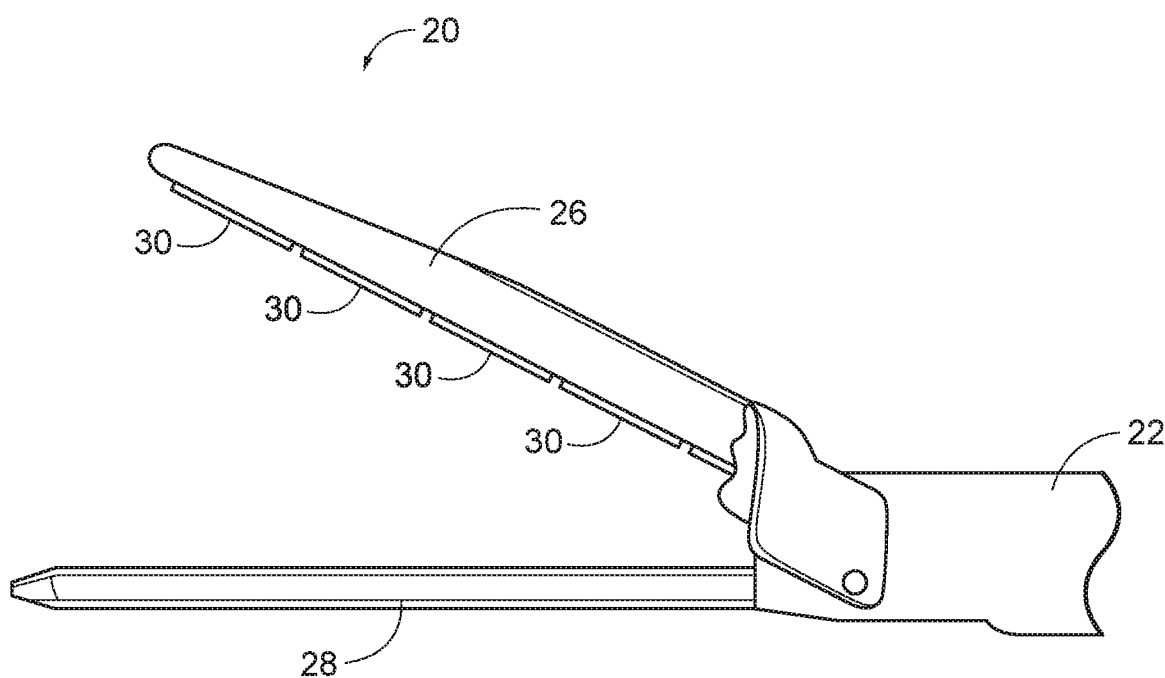
FIG. 2A depicts a side view of an end effector of the ultrasonic surgical instrument of FIG. 1 showing the end effector in an open configuration for receiving tissue of a patient.
Figure 2B:
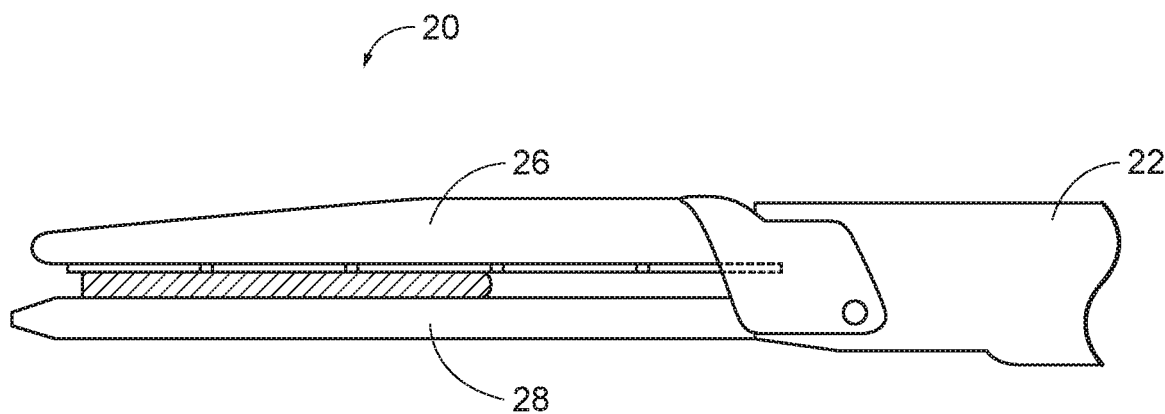
FIG. 2B depicts the side view of the end effector of FIG. 2A, but with the end effector in a closed configuration for clamping the tissue of the patient.

With reference to FIGS. 1-2B, handle assembly (18) further includes a trigger (48) operatively connected to clamp arm (26). Trigger (48) and clamp arm (26) are generally biased toward the unactuated, open configuration. However, selectively manipulating trigger (48) proximally pivots clamp arm (26) toward ultrasonic blade (28) from the open position to the closed position. As used in the present example, clamp arm (26) and ultrasonic blade (28) may also be generally referred to respectively as upper and lower jaws of surgical instrument (12). In the open position, clamp arm (26) and ultrasonic blade (28) are configured to receive the tissue, whereas clamp arm (26) is configured to clamp tissue against ultrasonic blade (28) for grasping, sealing, and/or cutting the tissue.

Ultrasonic blade (28) ultrasonically vibrates to seal and/or cut the tissue, whereas RF electrodes (30) provide electrical power to the tissue. RF electrodes (30) of the present example are all electrically similar electrodes with ultrasonic blade (28) also electrically connected as a return electrode. As used therein, the term "electrode" may thus apply to both RF electrodes (30) and ultrasonic blade (28) with respect to the RF electrical circuit. Without tissue, the electrical circuit from RF electrodes (30) to ultrasonic blade (28) is open, whereas the electrical circuit is closed by the tissue between RF electrode (30) and ultrasonic blade (28) in use. RF electrodes (30) may be activated to apply RF energy alone or in combination with ultrasonic activation of ultrasonic blade (28). For example, activating only RF electrodes (30) to apply RF energy alone may be used for spot coagulating without concern for inadvertently cutting tissue with ultrasonically activated ultrasonic blade (28). However, the combination of ultrasonic energy and RF energy may be used for sealing and/or cutting tissue to achieve any combination of diagnostic or therapeutic effects, various examples of which will be described below in greater detail.

As noted above, generator (14) is a single output generator that can deliver power through a single port to provide both RF and ultrasonic energy such that these signals can be delivered separately or simultaneously to end effector (20) for cutting and/or sealing tissue. Such a single output port generator (14) has a single output transformer with multiple taps to provide power, either for RF or for ultrasonic energy, to end effector (20) depending on the particular treatment being performed on the tissue. For example, generator (14) may deliver energy with higher voltage and lower current to drive ultrasonic transducer (24), with lower voltage and higher current as required to drive RF electrodes (30) for sealing tissue, or with a coagulation waveform for spot coagulation using either monopolar or bipolar electrosurgical electrodes. The output waveform from generator (14) can be steered, switched, or filtered to provide the desired frequency to end effector (20) of surgical instrument (12).

Figure 3:
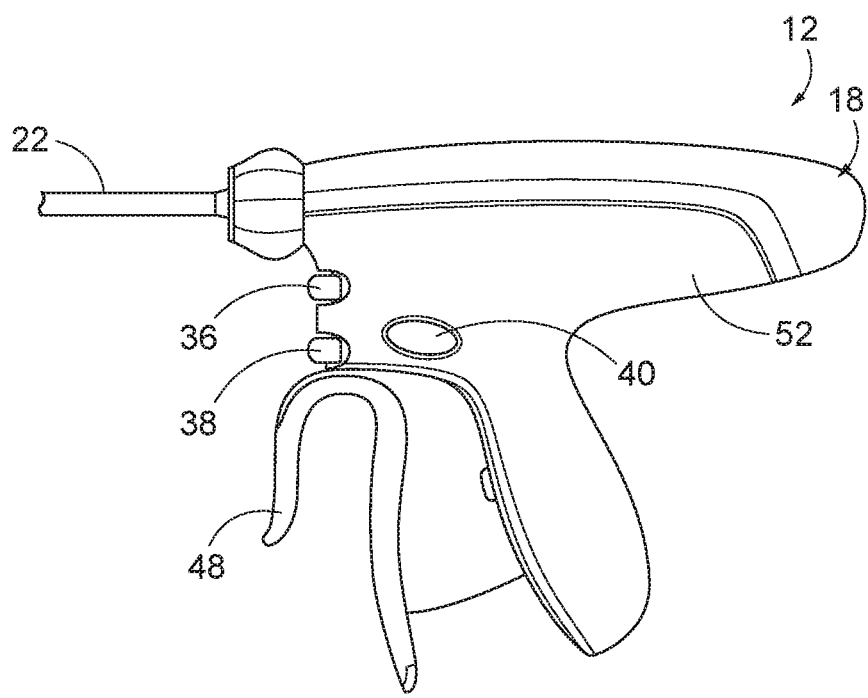
FIG. 3 depicts an enlarged side view of the handle assembly of FIG. 1.
Figure 4A:
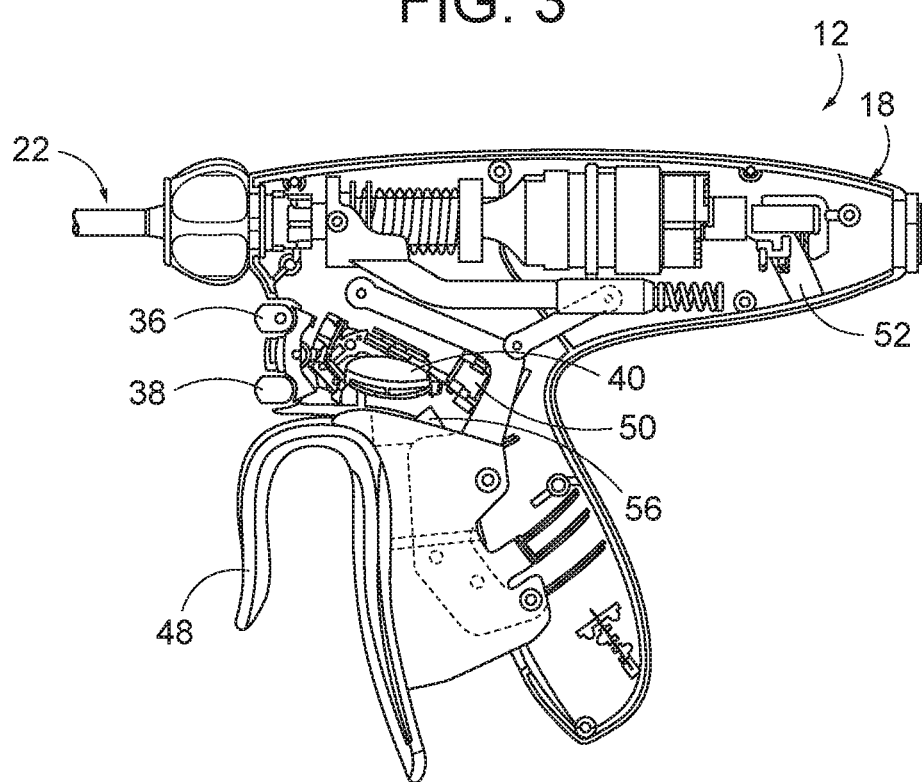
FIG. 4A depicts an enlarged side view of the handle assembly of FIG. 3 having various components removed for greater clarity of a trigger and a trigger switch in the open configuration.
Figure 4B:
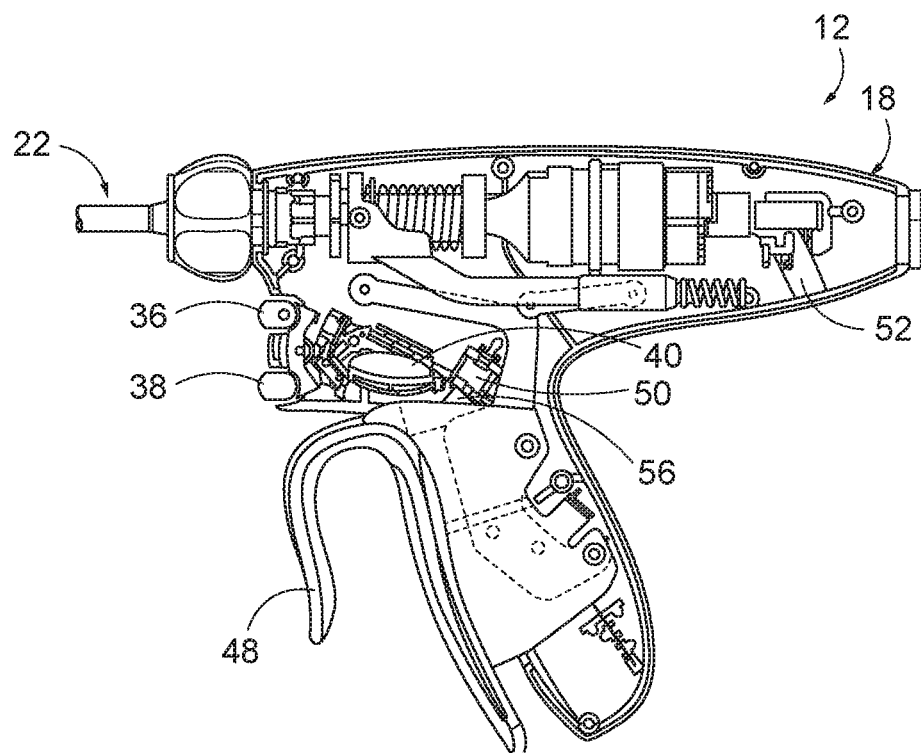
FIG. 4B depicts the enlarged side view of the handle assembly of FIG. 3, but showing the trigger and the trigger switch in the closed configuration.
Figure 5:
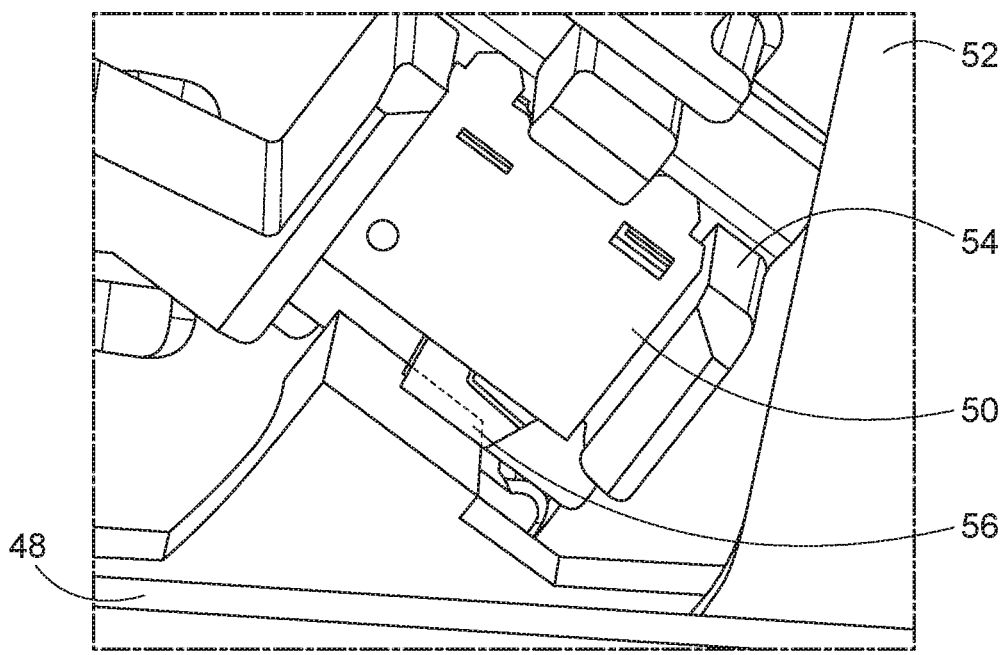
FIG. 5 depicts an enlarged perspective view of the trigger switch of FIG. 4B.

FIGS. 3-4B illustrate additional features of handle assembly (18), particularly with respect to trigger (48). Handle assembly (18) shown in FIG. 4A-5 includes a trigger input switch (50) mounted within a handle housing (52) to a securement flange (54). Trigger (48) also includes an input boss (56) extending upwardly and proximally therefrom toward trigger input switch (50). Input boss (56) cooperatively engages trigger input switch (50), which is operatively connected to controller (46) (see FIG. 1), to actuate trigger input switch (50) and thereby communicate the position of trigger (48). In the present example, the position of trigger (48) correlates to a position of clamp arm (26) and, more particularly, to the closed position of clamp arm (26). Actuation of input switch (50) by input boss (56) thus communicates to controller (46) that clamp arm (26) is in the closed position and may direct ultrasonic and/or RF energy. While input boss (56) and trigger input switch (50) are configured to correlate to the closed position, alternative positioning may also be used to the extent that the invention is not intended to be unnecessarily limited to actuation of trigger input switch (50) by trigger (48) in the closed position of the closed configuration.

Figure 6:
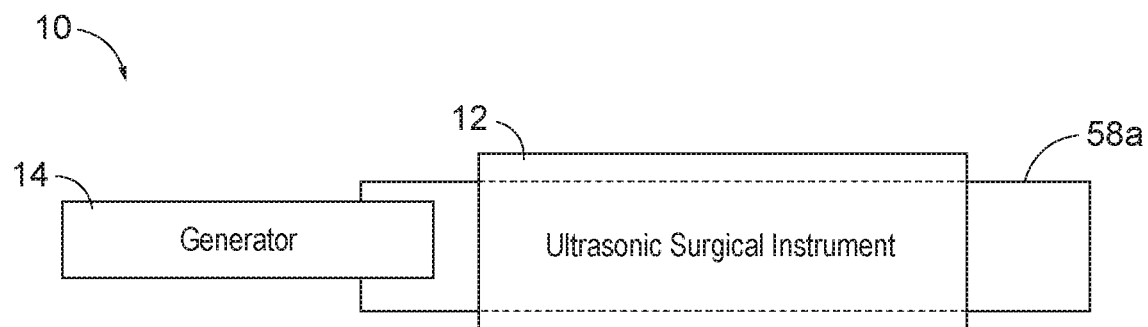
FIG. 6 depicts a schematic view of the ultrasonic surgical instrument of FIG. 1 in a closed short electrical state.
Figure 7:
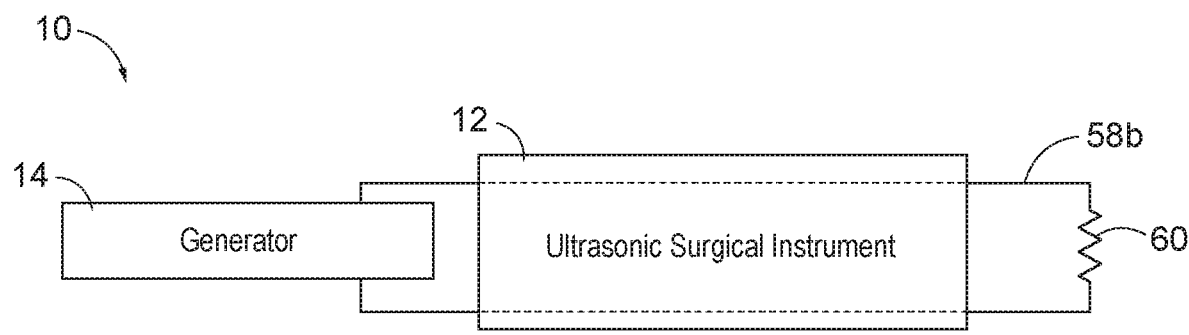
FIG. 7 depicts a schematic view of the ultrasonic surgical instrument of FIG. 1 in a closed resistive electrical state.
Figure 8:
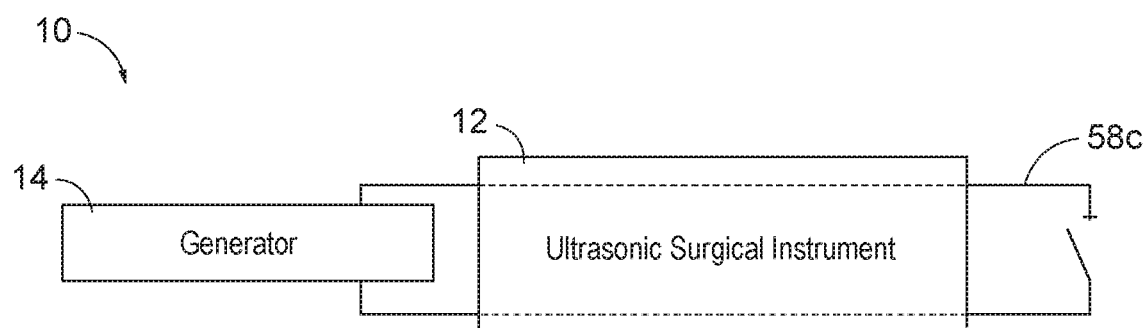
FIG. 8 depicts a schematic view of the ultrasonic surgical instrument of FIG. 1 in an open electrical state.

Controller (46) is further configured to identify the state of tissue between clamp arm (26) and ultrasonic blade (28) by measuring and monitoring RF impedance of tissue between RF electrodes (30) and ultrasonic blade (28). FIG. 6 schematically illustrates a closed short electrical state of an RF electrical circuit (58a) that occurs with direct electrical communication from one or more electrodes (30) to ultrasonic blade (30). Such direct electrical communication may also be referred to as an "electrical short" and occurs when an electrically conductive item (e.g., a metallic instrument) is clamped between clamp arm (26) and ultrasonic blade (28) and/or when a clamp pad on clamp arm (26) has deteriorated to a point where ultrasonic blade (28) directly contacts electrodes (30) when clamp arm (26) is in a closed position. functionally deteriorated. In any case, direct electrical communication results in a minimal RF impedance measurement, such as 0 ohms. In contrast, FIG. 7 schematically illustrates a closed resistive electrical state of an RF electrical circuit (58b) that occurs when tissue is positioned between RF electrodes (30) and ultrasonic blade (28). The tissue, schematically shown as a resistor (60) in FIG. 7 will generate a measurable RF impedance measurement greater than the minimal RF impedance measurement, and may change as one or both of ultrasonic and RF energies are applied to the tissue. FIG. 8 schematically illustrates, an open electrical state of an RF electrical circuit (58c) that occurs with no electrical communication from RF electrodes (30) to ultrasonic blade (28). Such lack of electrical communication may occur without tissue or direct contact between RF electrodes (30) and ultrasonic blade (28) and tends to result in an exceedingly high and/or RF impedance measurement that is essentially infinite for all practical purposes (e.g., greater than 3,000 ohms) or essentially an inability to effectively measure RF impedance due to the open electrical state.

Figure 9:
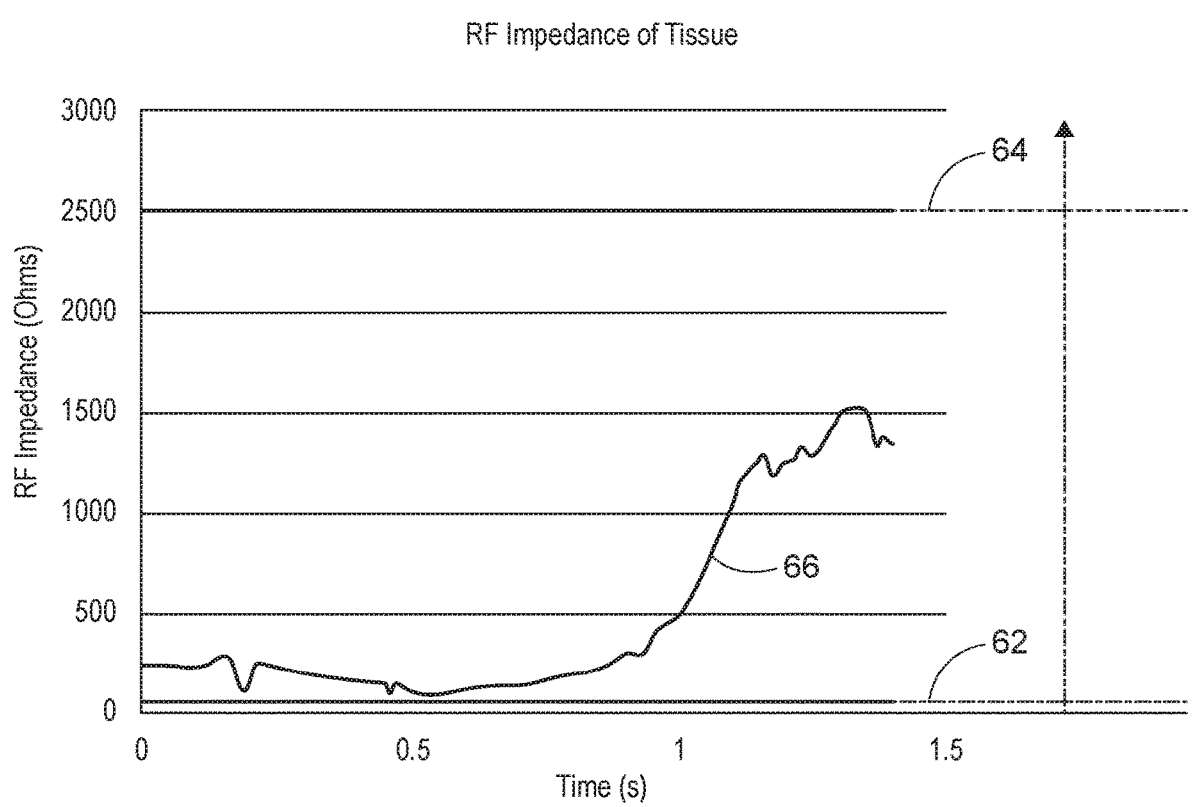
FIG. 9 depicts graph of an RF impedance measurement over time of the tissue sealed with the ultrasonic surgical instrument of FIG. 1.

Controller (46) is configured to monitor measured RF impedance between RF electrodes (30) and ultrasonic blade (28) and, based on this measured RF impedance, identify the presence of tissue between RF electrodes (30) and ultrasonic blade (28). FIG. 9, in conjunction with FIGS. 6-8, illustrates conditions for such identification stored to controller (46) and monitored in real-time. By way of example, a lower impedance threshold (62), such as 50 ohms, and an upper impedance threshold (64), such as 2500 ohms, is stored to controller (46) and compared against the measured RF impedance between RF electrodes (30) and ultrasonic blade (28) in use. Measured RF impedance below lower impedance threshold (62) correlates to the closed short electrical circuit (58a), whereas measured RF impedance above upper impedance threshold (64) correlates to the open electrical circuit (58c). In contrast, measured RF impedance between lower and upper impedance thresholds (62, 64), also referred to herein as intermediate RF impedance, correlates to the presence of tissue as shown in RF electrical circuit (58b).

One example of real-time intermediate RF impedance (66) in use is shown in FIG. 9. Such identifications of below, intermediate, and above RF impedance values that correlate to the presence or lack of tissue provide an RF impedance input to controller (46) for directing ultrasonic and/or RF energy, which will be discussed below in greater detail. While such measurement, monitoring, and processing is generally described above as performed by controller (46), it will be appreciated that any known internal logic may be used. The term "controller" is thus not intended to unnecessarily limit the invention described herein and broadly refers to any combination of software and hardware for such use.

While the teachings herein are provided in the context of instrument (12) described above, it should be understood that the teachings herein may be readily applied to various other kinds of instruments, including but not limited to instruments described in patent references cited herein. As another merely illustrative example, the teachings herein may be readily applied to any of the various instruments described in U.S. Provisional Patent App. No. 62/509,351, entitled "Ultrasonic Instrument with Electrosurgical Features," filed on May 22, 2017, the disclosure of which is incorporated by reference herein.

C. Exemplary Ultrasonic Energy and RF Energy Activations

Surgical system (10) of the present example shown in FIGS. 1-9 has a plurality of energy inputs discussed above, such as input device (32), upper button (36), lower button (38), side button (40), and trigger input switch (50), and RF impedance input based on RF electrical circuit (58a, 58b, 58c). These energy inputs are monitored by controller (46), which communicates with generator (14) to direct one or both ultrasonic and RF energy outputs respective to ultrasonic blade (28) and RF electrodes (30) for cutting and/or sealing tissue. To this end, predetermined energy inputs, of a variety of combinations, yield predetermined energy outputs according to a predetermined drive function specifically directed to desirable diagnostic or therapeutic effects on the tissue.

The following describes one example of predetermined energy outputs of a predetermined drive function initiated by one of upper button (36), lower button (38), and side button (40) in conjunction with other energy inputs monitored by controller (46). Based on these energy inputs, controller (46) directs generator (14) activation or deactivation of ultrasonic and/or RF energy according to the following predetermined energy outputs. While selective actuation of upper button (36), lower button (38), or side button (40) is described as initiating, it will be appreciated alternative actuations that may be so used for directing predetermined energy outputs. Furthermore, the collection of upper button (36), lower button (38), side button (40), and controller (46) are configured such that only one of upper button (36), lower button (38), and side button (40) may be actuated and communicated to controller (46) at a time for directing the predetermined energy outputs. In the event that more than one of upper button (36), lower button (38), and side button (40) are selectively actuated by the clinician, only the first of these will be communicated to controller (46) for directing the predetermined energy outputs. In alternative examples, more than one of upper button (36), lower button (38), and side button (40) may be actuated and communicated to controller (46) for achieving alternative predetermined energy outputs.

With respect to selective actuation of upper button (36), controller (46) further monitors input device (32) of generator (14), trigger input switch (50), and the RF impedance state of measurements as below, above, or intermediate as discussed above. Based on these predetermined inputs, the following predetermined energy outputs of ultrasonic and RF energies are directed by controller (46). For example, actuating upper button (36) with input device (32) set to ultrasonic energy only results in controller (46) ignoring trigger input switch (50) and the RF impedance state and directing ultrasonic blade (28) to activate while RF electrodes remain inactive. In another example, actuating upper button (36) with input device (32) set to combined ultrasonic and RF energies results in controller (46) monitoring trigger input switch (50) and the RF impedance state. With trigger input switch (50) actuated and the RF impedance state below lower impedance threshold (62), controller (46) transducer (24) to activate ultrasonic blade (28) ultrasonically while RF electrodes (30) remain inactive. Remaining exemplary predetermined energy inputs with exemplary predetermined energy outputs are detailed below in Table 1 for actuation of upper button (36).

TABLE 1

Predetermined Energy Output for Upper Button

| Input in Addition to Upper Button Actuation | | | Energy Output | |
| --- | --- | --- | --- | --- |
| Generator Input Device | Trigger Input Switch | RF Impedance Input State | Ultra-sonic Energy | RF Energy |
| Ultrasonic Energy Only | N/A | N/A | Active | Inactive |
| Ultrasonic and RF Energies | Actuated | Below | Active | Inactive |
| Ultrasonic and RF Energies | Actuated | Intermediate | Active | Active |
| Ultrasonic and RF Energies | Actuated | Above | Active | Inactive |
| Ultrasonic and RF Energies | Unactuated | Below | Inactive | Inactive |
| Ultrasonic and RF Energies | Unactuated | Intermediate | Active | Active |
| Ultrasonic and RF Energies | Unactuated | Above | Active | Inactive |

With respect to selective actuation of lower button (38), controller (46) ignores input device (32) of generator (14) while monitoring trigger input switch (50) and the RF impedance state of measurements as below, above, or intermediate as discussed above. Based on these predetermined inputs, the following predetermined energy outputs of ultrasonic and RF energies are directed by controller (46). For example, actuating lower button (38) with controller (46) monitoring trigger input switch (50) as actuated and RF impedance state as below results in controller (46) directing transducer (24) (and, hence, ultrasonic blade (28)) and RF electrodes (30) to remain inactive. Remaining exemplary predetermined energy inputs with exemplary predetermined energy outputs are detailed below in Table 2 for actuation of lower button (38).

TABLE 2

Predetermined Energy Output for Lower Button

Input in Addition to Lower Button Actuation

| Generator | Trigger | | Energy Output | |
|---|---|---|---|---|
| Input Device | Input Switch | RF Impedance Input State | Ultrasonic Energy | RF Energy |
| N/A | Actuated | Below | Inactive | Inactive |
| N/A | Actuated | Intermediate | Active | Active |
| N/A | Actuated | Above | Active | Active |
| N/A | Unactuated | N/A | Inactive | Inactive |

With respect to selective actuation of side button (38), controller (46) ignores input device (32) of generator (14) while monitoring trigger input switch (50) and the RF impedance state of measurements as below, above, or intermediate as discussed above. Based on these predetermined inputs, the following predetermined energy outputs of ultrasonic and RF energies are directed by controller (46). For example, actuating side button (38) with controller (46) monitoring trigger input switch (50) as actuated and RF impedance state as below results in controller (46) directing transducer (24) (and, hence, ultrasonic blade (28)) and RF electrodes (30) to remain inactive. Remaining exemplary predetermined energy inputs with exemplary predetermined energy outputs are detailed below in Table 3 for actuation of side button (38).

TABLE 3

Predetermined Energy Output for Side Button

Input in Addition to Side Toggle Button Actuation

| Generator | Trigger | | Energy Output | |
|---|---|---|---|---|
| Input Device | Input Swich | RF Impedance Input State | Ultrasonic Energy | RF Energy |
| N/A | Actuated | Below | Inactive | Inactive |
| N/A | Actuated | Intermediate | Active | Active |
| N/A | Actuated | Above | Inactive | Inactive |
| N/A | Unactuated | N/A | Inactive | Inactive |

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic surgical instrument, comprising: (a) an end effector configured to actuate from a first configuration to a second configuration, the end effector including: (i) an ultrasonic blade configured to be selectively driven to apply an ultrasonic energy to a tissue, and (ii) an RF electrode configured to be selectively driven to apply RF energy to the tissue, wherein the RF electrode is further configured to measure a tissue impedance of the tissue engaged by the end effector; (b) a shaft assembly projecting proximally from the end effector; (c) a body projecting proximally from the shaft assembly, wherein the body includes: (i) a first ultrasonic energy input operatively connected to the ultrasonic blade, wherein the first ultrasonic energy input is configured to be selectively actuated from a first unactuated energy input state to a first actuated energy input state, (ii) a trigger operatively connected to the end effector and configured to selectively actuate the end effector from the first configuration to the second configuration, and (iii) a trigger input operatively connected to the trigger, wherein the trigger input is configured to be actuated from an unactuated trigger input state in the first configuration to an actuated trigger input state in the second configuration; and (d) a power controller operatively connected to the ultrasonic blade, the RF electrode, the first ultrasonic energy input, and the trigger input, wherein the power controller is configured to direct activation of at least one of the ultrasonic blade or the RF electrode according to a predetermined drive function based on the tissue impedance, the state of the first energy input, and the state of the trigger input.

Example 2

The ultrasonic surgical instrument of Example 1, wherein the power controller is further configured to direct activation of the ultrasonic blade to deliver ultrasonic energy according to the predetermined drive function.

Example 3

The ultrasonic surgical instrument of claim 2, wherein the power controller is further configured to prevent activation of the RF electrode according to the predetermined drive function.

Example 4

The ultrasonic surgical instrument of Example 2, wherein the power controller is further configured to direct activation of the RF electrode to deliver RF energy according to the predetermined drive function.

Example 5

The ultrasonic surgical instrument of Example 4, wherein the power controller is further configured to simultaneously direct activation of the ultrasonic blade and the RF electrode to deliver ultrasonic energy and the RF energy, respectively, according to the predetermined drive function.

Example 6

The ultrasonic surgical instrument of Example 1, wherein the power controller is configured to direct activation of the RF electrode to deliver RF energy according to the predetermined drive function.

Example 7

The ultrasonic surgical instrument of any one or more of Examples 1 through 6, further comprising a second ultrasonic energy input operatively connected to the ultrasonic blade and the power controller, wherein the second ultrasonic energy input is configured to be selectively actuated from a second unactuated energy input state to a second actuated energy input state, and wherein the power controller is further configured to direct activation of the ultrasonic blade and the RF electrode according to the predetermined drive function based on the tissue impedance, the state of the first energy input, the state of the trigger input, and the state of the second energy input.

Example 8

The ultrasonic surgical instrument of Example 7, wherein the first ultrasonic energy input in the first actuated ultrasonic energy input state is configured to activate the ultrasonic blade with a maximum ultrasonic energy, and wherein the second ultrasonic energy input in the second actuated ultrasonic energy input state is configured to activate the ultrasonic blade with a lesser ultrasonic energy.

Example 9

The ultrasonic surgical instrument of any one or more of Examples 7 through 8, wherein the first or second ultrasonic energy inputs are configured such that the first and second ultrasonic energy inputs cannot be simultaneously actuated.

Example 10

The ultrasonic surgical instrument of any one or more of Examples 7 through 9, further comprising a third ultrasonic energy input operatively connected to the ultrasonic blade and the power controller, wherein the third ultrasonic energy input is configured to be selectively actuated from a second unactuated energy input state to a second actuated energy input state, and wherein the power controller is further configured to direct activation of the ultrasonic blade and the RF electrode according to the predetermined drive function based on the tissue impedance, the state of the first energy input, the state of the trigger input, the state of the second energy input, and the state of the third energy input.

Example 11

The ultrasonic surgical instrument of Example 10, wherein the third ultrasonic energy input in the third actuated ultrasonic energy input state is configured to activate the ultrasonic blade with a pulsed ultrasonic energy.

Example 12

The ultrasonic surgical instrument of any one or more of Examples 10 through 11, wherein the first, second, or third ultrasonic energy inputs are configured such that the first, second, and third ultrasonic energy inputs cannot be simultaneously actuated.

Example 13

The ultrasonic surgical instrument of any one or more of Examples 1 through 12, further comprising a generator configured to generate the ultrasonic energy and the RF energy.

Example 14

The ultrasonic surgical instrument of any one or more of Examples 1 through 13, wherein the power controller is further configured to determine whether the measured tissue impedance is below a lower impedance threshold, above an upper impedance threshold, or intermediate between the lower and upper impedance thresholds.

Example 15

The ultrasonic surgical instrument of Example 14, wherein the power controller is further configured to direct activation of the at least one of the ultrasonic blade or the RF electrode according to the predetermined drive function based on the identified tissue impedance being below the lower impedance threshold, above the upper impedance threshold, or intermediate between the lower and upper impedance thresholds.

Example 16

An ultrasonic surgical instrument, comprising: (a) an end effector configured to actuate from a first configuration to a second configuration, including: (i) an ultrasonic blade configured to be selectively driven to apply ultrasonic energy to the tissue, (ii) an RF electrode configured to be selectively driven to apply RF energy to the tissue, wherein the RF electrode is further configured to measure a tissue impedance of the tissue clamped within the end effector; (b) a shaft assembly projecting proximally from the end effector; (c) a body projecting proximally from the shaft assembly, wherein the body includes: (i) a first ultrasonic energy input operatively connected to the ultrasonic blade, wherein the first ultrasonic energy input is configured to be selectively actuated from a first unactuated energy input state to a first actuated energy input state, (ii) a second ultrasonic energy input operatively connected to the ultrasonic blade and the power controller, wherein the second ultrasonic energy input is configured to be selectively actuated from a second unactuated energy input state to a second actuated energy input state, and (iii) a trigger input configured to be actuated from an unactuated trigger input state in the first configuration to an actuated trigger input state in the second configuration; and (d) a power controller operatively connected to the ultrasonic blade, the RF electrode, the first ultrasonic energy input, the second ultrasonic energy input, and the trigger input, wherein the power controller is configured to determine the measured tissue impedance as below a lower impedance threshold, above an upper impedance threshold, or intermediate between the lower and upper impedance thresholds, and wherein the power controller is further configured to direct activation of at least one of the ultrasonic blade or the RF electrode according to a predetermined drive function based on the state of the first ultrasonic energy input, the state of the second ultrasonic energy input, the state of the trigger input, and the identified tissue impedance being below the lower impedance threshold, above the upper impedance threshold, or intermediate between the lower and upper impedance thresholds.

Example 17

The ultrasonic surgical instrument of Example 16, wherein the first or second ultrasonic energy inputs are configured such that the first and second ultrasonic energy inputs cannot be simultaneously actuated.

Example 18

A method of energizing a surgical instrument including an ultrasonic blade and an RF electrode respectively configured to deliver an ultrasonic energy and an RF energy to the tissue, wherein the surgical instrument includes a first ultrasonic energy input, a trigger input, and a power controller, wherein the first ultrasonic energy input is operatively connected to the ultrasonic blade, wherein the first ultrasonic energy input is configured to be selectively actuated from a first unactuated energy input state to a first actuated energy input state, wherein the trigger input is configured to be actuated from an unactuated trigger input state in the first configuration to an actuated trigger input state in the second configuration, wherein the power controller is operatively connected to the ultrasonic blade, the RF electrode, the first ultrasonic energy input, and the trigger input, the method comprising: (a) determining, with the power controller, whether the first ultrasonic energy input is in the first unactuated energy input state or the first actuated energy input state; (b) determining, with the power controller, whether the trigger input is in the unactuated trigger input state or the actuated trigger input state; (c) interrogating the tissue with an electrical signal via at least one of the ultrasonic blade or the RF electrode to measure a tissue impedance of the tissue via the power controller; and (d) selectively driving at least one of the ultrasonic blade or the RF electrode according to a predetermined drive function based on the determined state of the first ultrasonic energy input, the determined state of the trigger input, and the measured tissue impedance.

Example 19

The method of Example 18, further comprising determining whether the measured tissue impedance is below a lower impedance threshold, above an upper impedance threshold, or intermediate between the lower and upper impedance thresholds.

Example 20

The method of any one or more of Examples 18 through 19, wherein the surgical instrument further includes a second ultrasonic energy input operatively connected to the ultrasonic blade and the power controller, wherein the second ultrasonic energy input is configured to be selectively actuated from a second unactuated energy input state to a second actuated energy input state, wherein the method further comprises: (a) determining, with the power controller, whether the second energy input is in the second unactuated energy input state or the second actuated energy input state; and (b) selectively driving at least one of the ultrasonic blade or the RF electrode according to a predetermined drive function based on the determined state of the first ultrasonic energy input, the determined state of the trigger input, the measured tissue impedance, and determined state of the second energy input.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of any claims.

Any one or more of the teaching, expressions, embodiments, examples, etc. described herein may be combined with any one or more of the teachings, expressions, embodiments, examples, etc. described in U.S. patent application Ser. No. 15/967,763, entitled "Combination Ultrasonic and Electrosurgical Instrument with Adjustable Energy Modalities and Method for Sealing Tissue and Inhibiting Tissue Resection," filed on May 1, 2018, published as U.S. Pub. No. 2018/0333185 on Nov. 22, 2018; U.S. patent application Ser. No. 15/967,770, entitled "Combination Ultrasonic and Electrosurgical Instrument with Adjustable Clamp Force and Related Methods," filed on May 1, 2018, Published as U.S. Pub. No. 2018/0333187 on Nov. 22, 2018; U.S. patent application Ser. No. 15/967,775, entitled "Combination Ultrasonic and Electrosurgical Instrument with Adjustable Energy Modalities and Method for Limiting Blade Temperature," filed on May 1, 2018, published as U.S. Pub. No. 2018/0333188 on Nov. 22, 2018; U.S. patent application Ser. No. 15/967,777, entitled "Combination Ultrasonic and Electrosurgical Instrument and Method for Sealing Tissue with Various Termination Parameters," filed on May 1, 2018, published as U.S. Pub. No. 2018/0333189 on Nov. 22, 2018; and/or U.S. patent application Ser. No. 15/967,784, entitled "Combination Ultrasonic and Electrosurgical Instrument and Method for Sealing Tissue in Successive Phases," filed on May 1, 2018, published as U.S. Pub. No. 2018/0333190 on Nov. 22, 2018. The disclosure of each of these applications is incorporated by reference herein.

Further, any one or more of the teachings, expressions, embodiments, examples, etc. described herein may be combined with any one or more of the teachings, expressions, embodiments, examples, etc. described in U.S. patent application Ser. No. 15/967,740, entitled "Combination Ultrasonic and Electrosurgical Instrument Having Electrical Circuits With Shared Return Path," filed on May 1, 2018, published as U.S. Pub. No. 2018/0333177 on Nov. 22, 2018; U.S. patent application Ser. No. 15/967,746, entitled "Combination Ultrasonic and Electrosurgical Instrument Having Slip Ring Electrical Contact Assembly," filed on May 1, 2018, issued as U.S. Pat. No. 10,945,788 on Mar. 16, 2021; U.S. patent application Ser. No. 15/967,747, entitled "Combination Ultrasonic and Electrosurgical Instrument Having Electrically Insulating Features," filed on evert-date-herewith May 1, 2018, issued as U.S. Pat. No. 10,945,779 on Mar. 16, 2021; U.S. patent application Ser. No. 15/967,751, entitled "Combination Ultrasonic and Electrosurgical Instrument Having Curved Ultrasonic Blade," filed on May 1, 2018, issued as U.S. Pat. No. 11,033,316 on Jun. 15, 2021; U.S. patent application Ser. No. 15/967,753, entitled "Combination Ultrasonic and Electrosurgical Instrument Having Clamp Arm Electrode," filed on May 1, 2018, issued as U.S. Pat. No. 11,058,472 on Jul. 13, 2021; U.S. patent application Ser. No. 15/967,759, entitled "Combination Ultrasonic and Electrosurgical Instrument Having Ultrasonic Waveguide With Distal Overmold Member," filed on May 1, 2018, issued as U.S. Pat. No. 11,051,866 on Jul. 6, 2021; U.S. patent application Ser. No. 15/967,761, entitled "Combination Ultrasonic and Electrosurgical System Having Generator Filter Circuitry," filed on May 1, 2018, published as U.S. Pat. No. 2018/0333184 on Nov. 22, 2018; and/or U.S. patent application Ser. No. 15/967,764, entitled "Combination Ultrasonic and Electrosurgical System Having EEPROM and ASIC Components," filed on May 1, 2018, published as U.S. Pub. No. 2018/0333186 on Nov. 22, 2018, issued as U.S. Pat. No. 11,129,661 on Sep. 28, 2021. The disclosure of each of these applications is incorporated by reference herein.

Further, any one or more of the teachings, expressions, embodiments, examples, etc. described herein may be combined with any one or more of the teachings, expressions, embodiments, examples, etc. described in U.S. Pat. App. No. 15/967,740, entitled "Combination Ultrasonic and Electrosurgical Instrument Having Electrical Circuits With Shared Return Path," filed on May 1, 2018, published as U.S. Pub. No. 2018/0333177 on Nov. 22, 2018; U.S, Pat. App. No. 15/967,746, entitled "Combination Ultrasonic and Electrosurgical Instrument Having Slip Ring Electrical Contact Assembly," filed on May 1, 2018, issued as U.S. Pat. No. 10,945,788 on Mar. 16, 2021; U.S. Pat. App. No. 15/967, 747, entitled "Combination Ultrasonic and Electrosurgical Instrument Having Electrically Insulating Features," filed on May 1, 2018, issued as U.S. Pat. No. 10,945,779 on Mar. 16, 2021; U.S. Pat. App. No. 15/967,751, entitled "Combination Ultrasonic and Electrosurgical instrument Having Curved Ultrasonic Blade," filed on May 1, 2018, issued as U.S. Pat. No. 11,033,316 on Jun. 15, 2021; U.S. Pat. App. No. 15/967,753, entitled "Combination Ultrasonic and Electrosurgical instrument Having Clamp Arm Electrode," filed on May 1, 2018, issued as U.S. Pat. No. 11,058,472 on Jul. 13, 2021; U.S. Pat. App. No. 15/967,759, entitled "Combination Ultrasonic and Electrosurgical Instrument Having Ultrasonic Waveguide With Distal Overmold Member," filed on May 1, 2018, issued as U.S. Pat. No. 11,051,866 on Jul. 6, 2021; U.S. Pat. App. No. 15/967,761, entitled "Combination Ultrasonic and Electrosurgical System Having Generator Filter Circuitry," filed on May 1, 2018, published as U.S. Pat. No. 2018/0333184 on Nov. 22, 2018; and/or U.S. Pat. App. No, 15/967,764, entitled "Combination Ultrasonic and Electrosurgical System Having EEPROM and ASIC Components," filed on May 1, 2018, published as U.S. Pub. No. 2018/0333186 on Nov. 22, 2018, issued as U.S. Pat. No. 11,129,661 on Sep. 28, 2021. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use.

Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a clinician immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention is understood not to be limited to the details of structure and operation shown and described in the specification and drawings.

I claim:

1. An ultrasonic surgical instrument, comprising:
    (a) an end effector configured to actuate from a first configuration to a second configuration, the end effector including:
        (i) an ultrasonic blade configured to be selectively driven to apply an ultrasonic energy to a tissue, and
        (ii) an RF electrode configured to be selectively driven to apply RF energy to the tissue, wherein the RF electrode is further configured to measure a tissue impedance of the tissue engaged by the end effector;
    (b) a shaft assembly projecting proximally from the end effector;
    (c) a body projecting proximally from the shaft assembly, wherein the body includes:
        (i) a first ultrasonic energy input operatively connected to the ultrasonic blade, wherein the first ultrasonic energy input is configured to be selectively actuated from a first unactuated energy input state to a first actuated energy input state,
        (ii) a trigger operatively connected to the end effector and configured to selectively actuate the end effector from the first configuration to the second configuration, and
        (iii) a trigger input operatively connected to the trigger, wherein the trigger input is configured to be actuated from an unactuated trigger input state in the first configuration to an actuated trigger input state in the second configuration; and
    (d) a power controller operatively connected to the ultrasonic blade, the RF electrode, the first ultrasonic energy input, and the trigger input, wherein the power controller is configured to direct activation of at least a portion of the end effector according to a predetermined drive function based on the tissue impedance, the state of the first energy input, and the state of the trigger input, and
        wherein the power controller includes a lower impedance threshold and an upper impedance threshold stored thereon, wherein the power controller is further configured to determine whether the measured tissue impedance is below the lower impedance threshold thereby correlating to a first electrical state, above the upper impedance threshold thereby correlating to a second electrical state, or intermediate between the lower and upper impedance thresholds thereby indicative of a third electrical state, and
        wherein the power controller is further configured to initiate and direct activation of the at least the portion of the end effector according to the predetermined drive function based on the identified tissue impedance being below the lower impedance threshold.

2. The ultrasonic surgical instrument of claim 1, wherein the power controller is further configured to direct activation of the ultrasonic blade to deliver ultrasonic energy according to the predetermined drive function.

3. The ultrasonic surgical instrument of claim 2, wherein the power controller is further configured to prevent activation of the RF electrode according to the predetermined drive function.

4. The ultrasonic surgical instrument of claim 2, wherein the power controller is further configured to direct activation of the RF electrode to deliver RF energy according to the predetermined drive function.

5. The ultrasonic surgical instrument of claim 4, wherein the power controller is further configured to simultaneously direct activation of the ultrasonic blade and the RF electrode to deliver ultrasonic energy and the RF energy, respectively, according to the predetermined drive function.

6. The ultrasonic surgical instrument of claim 1, wherein the power controller is configured to direct activation of the RF electrode to deliver RF energy according to the predetermined drive function.

7. The ultrasonic surgical instrument of claim 1, further comprising a second ultrasonic energy input operatively connected to the ultrasonic blade and the power controller, wherein the second ultrasonic energy input is configured to be selectively actuated from a second unactuated energy input state to a second actuated energy input state, and wherein the power controller is further configured to direct activation of the ultrasonic blade and the RF electrode according to the predetermined drive function based on the tissue impedance, the state of the first energy input, the state of the trigger input, and the state of the second energy input.

8. The ultrasonic surgical instrument of claim 7, wherein the first ultrasonic energy input in the first actuated ultrasonic energy input state is configured to activate the ultrasonic blade with a maximum ultrasonic energy, and wherein the second ultrasonic energy input in the second actuated ultrasonic energy input state is configured to activate the ultrasonic blade with a lesser ultrasonic energy.

9. The ultrasonic surgical instrument of claim 8, further comprising a third ultrasonic energy input operatively connected to the ultrasonic blade and the power controller, wherein the third ultrasonic energy input is configured to be selectively actuated from a second unactuated energy input state to a second actuated energy input state, and wherein the power controller is further configured to direct activation of the ultrasonic blade and the RF electrode according to the predetermined drive function based on the tissue impedance, the state of the first energy input, the state of the trigger input, the state of the second energy input, and the state of the third energy input.

10. The ultrasonic surgical instrument of claim 9, wherein the third ultrasonic energy input in the third actuated ultrasonic energy input state is configured to activate the ultrasonic blade with a pulsed ultrasonic energy.

11. The ultrasonic surgical instrument of claim 9, wherein the first, second, or third ultrasonic energy inputs are configured such that the first, second, and third ultrasonic energy inputs cannot be simultaneously actuated.

12. The ultrasonic surgical instrument of claim 7, wherein the first or second ultrasonic energy inputs are configured such that the first and second ultrasonic energy inputs cannot be simultaneously actuated.

13. The ultrasonic surgical instrument of claim 1, further comprising a generator configured to generate the ultrasonic energy and the RF energy.

14. The ultrasonic surgical instrument of claim 1, wherein the power controller is further configured to initiate and direct activation of the at least the portion of the end effector according to the predetermined drive function based on the identified tissue impedance being below the lower impedance threshold, above the upper impedance threshold, and intermediate between the lower and upper impedance thresholds.

15. The ultrasonic surgical instrument of claim 1, wherein the ultrasonic blade and the RF electrode at least partially define an electrical circuit, wherein the first electrical state with the measured tissue impedance below the lower impedance threshold is configured such that the electrical circuit is electrically shorted, wherein the second electrical state with the measured tissue impedance above the upper impedance threshold is configured such that the electrical circuit is electrically open, and wherein the third electrical state with the measured tissue impedance intermediate between the lower and upper impedance thresholds is configured such that the electrical circuit is electrically closed.

16. The ultrasonic surgical instrument of claim 1, wherein the power controller is configured to direct activation of at least one of the ultrasonic blade or the RF electrode according to the predetermined drive function based on the tissue impedance, the state of the first energy input, and the state of the trigger input, and wherein the power controller is further configured to initiate and direct activation of the at least one of the ultrasonic blade or the RF electrode according to the predetermined drive function based on the identified tissue impedance being above the upper impedance threshold.

17. The ultrasonic surgical instrument of claim 1, wherein the power controller is configured to direct activation of at least one of the ultrasonic blade or the RF electrode according to the predetermined drive function based on the tissue impedance, the state of the first energy input, and the state of the trigger input, and wherein the power controller is further configured to initiate and direct activation of the ultrasonic blade according to the predetermined drive function based on the identified tissue impedance being below the lower impedance threshold.

18. An ultrasonic surgical instrument, comprising:
(a) an end effector, including:
(i) an ultrasonic blade configured to be selectively driven to apply ultrasonic energy to a tissue,
(ii) a clamp arm configured to actuate relative to the ultrasonic blade from a first configuration toward a second configuration, wherein the clamp arm is configured to clamp the tissue against the ultrasonic blade in the second configuration, and
(iii) an RF electrode positioned on the clamp arm and configured to be selectively driven to apply RF energy to the tissue, wherein the RF electrode is further configured to measure a tissue impedance of the tissue clamped against the ultrasonic blade;
(b) a shaft assembly projecting proximally from the end effector;
(c) a body projecting proximally from the shaft assembly, wherein the body includes:
(i) a first ultrasonic energy input operatively connected to the ultrasonic blade, wherein the first ultrasonic energy input is configured to be selectively actuated from a first unactuated energy input state to a first actuated energy input state,
(ii) a second ultrasonic energy input configured to be selectively actuated from a second unactuated energy input state to a second actuated energy input state, and
(iii) a trigger input configured to be actuated from an unactuated trigger input state in the first configuration to an actuated trigger input state in the second configuration; and
(d) a power controller operatively connected to the ultrasonic blade and the second ultrasonic energy input, the RF electrode, the first ultrasonic energy input, the second ultrasonic energy input, and the trigger input, wherein the power controller is configured to determine the measured tissue impedance as below a lower impedance threshold in a first electrical state of the ultrasonic blade and the RF electrode, above an upper impedance threshold in a second electrical state of the ultrasonic blade and the RF electrode, or intermediate between the lower and upper impedance thresholds in a third electrical state of the ultrasonic blade and the RF electrode, and wherein the power controller is further configured to direct activation of at least a portion of the end effector according to a predetermined drive function based on the state of the first ultrasonic energy input, the state of the second ultrasonic energy input, the state of the trigger input, and the identified tissue impedance being below the lower impedance threshold, above the upper impedance threshold, or intermediate between the lower and upper impedance thresholds,
wherein the first electrical state is configured to indicate that the ultrasonic blade and the RF electrode are in direct electrical contact, wherein the second electrical state is configured to indicate that there is no direct electrical contact between the ultrasonic blade and the RF electrode and that there is no tissue in contact between the ultrasonic blade and the RF electrode, and wherein the third electrical state is configured to indicate that there is tissue in contact between the ultrasonic blade and the RF electrode, and
wherein the power controller is further configured to initiate and direct activation of the at least the portion of the end effector according to the predetermined drive function based respectively on each of the first, second, and third electrical states such that the at least the portion of the end effector activates in each of the first, second, and third electrical states.

19. The ultrasonic surgical instrument of claim 18, wherein the first or second ultrasonic energy inputs are configured such that the first and second ultrasonic energy inputs cannot be simultaneously actuated.

20. An ultrasonic surgical instrument, comprising:
(a) an end effector configured to actuate from a first configuration to a second configuration, the end effector including:
  (i) an ultrasonic blade configured to be selectively driven to apply an ultrasonic energy to a tissue, and
  (ii) an RF electrode configured to be selectively driven to apply RF energy to the tissue, wherein the RF electrode is further configured to measure a tissue impedance of the tissue engaged by the end effector;
(b) a shaft assembly projecting proximally from the end effector;
(c) a body projecting proximally from the shaft assembly, wherein the body includes:
  (i) a first ultrasonic energy input operatively connected to the ultrasonic blade, wherein the first ultrasonic energy input is configured to be selectively actuated from a first unactuated energy input state to a first actuated energy input state,
  (ii) a trigger operatively connected to the end effector and configured to selectively actuate the end effector from the first configuration to the second configuration, and
  (iii) a trigger input operatively connected to the trigger, wherein the trigger input is configured to be actuated from an unactuated trigger input state in the first configuration to an actuated trigger input state in the second configuration; and
(d) a power controller operatively connected to the ultrasonic blade, the RF electrode, the first ultrasonic energy input, and the trigger input, wherein the power controller is configured to direct activation of at least one of the ultrasonic blade or the RF electrode according to a predetermined drive function based on the tissue impedance, the state of the first energy input, and the state of the trigger input, and
wherein the power controller includes a lower impedance threshold and an upper impedance threshold stored thereon, wherein the power controller is further configured to determine whether the measured tissue impedance is below the lower impedance threshold thereby correlating to a first electrical state, above the upper impedance threshold thereby correlating to a second electrical state, or intermediate between the lower and upper impedance thresholds thereby indicative of a third electrical state, and
wherein the power controller is further configured to initiate and direct activation of the at least one of the ultrasonic blade or the RF electrode according to the predetermined drive function based on the identified tissue impedance being above the upper impedance threshold.

\* \* \* \* \*